United States Patent [19]

Kropf

[11] Patent Number: 4,760,849
[45] Date of Patent: Aug. 2, 1988

[54] PLANAR BLANK AND A COIL SPRING MANUFACTURED THEREFROM

[75] Inventor: Laurent Kropf, Penthaz, Switzerland

[73] Assignee: Medinvent S.A., Lausanne, Switzerland

[21] Appl. No.: 846,220

[22] Filed: Mar. 31, 1986

[30] Foreign Application Priority Data

Apr. 10, 1985 [SE] Sweden ................................ 8501762

[51] Int. Cl.⁴ ............................................. A61M 29/00
[52] U.S. Cl. .................................... 128/341; 128/343; 128/334 R; 604/104
[58] Field of Search .................... 128/341, 345, 334 R, 128/1 R; 604/104, 106, 49; 267/61 R, 166, 180, 181; 29/173; 428/542.8

[56] References Cited

U.S. PATENT DOCUMENTS

| | | | |
|---|---|---|---|
| 171,157 | 12/1875 | Mitchell | 29/173 |
| 1,905,103 | 4/1933 | Johnson | 267/180 |
| 4,306,318 | 12/1981 | Mano et al. | 128/334 R |
| 4,377,280 | 3/1983 | Wienand et al. | 267/180 |
| 4,503,569 | 3/1985 | Dotter | 128/334 R |
| 4,553,545 | 11/1985 | Maass et al. | 604/104 |
| 4,653,496 | 3/1987 | Bundy et al. | 604/49 |

*Primary Examiner*—C. Fred Rosenbaum
*Assistant Examiner*—H. Macey
*Attorney, Agent, or Firm*—Burns, Doane, Swecker & Mathis

[57] ABSTRACT

A planar blank is provided which permits the manufacture of a coil spring suitable for implantation. The blank has an elongated, essentially straight mid section which at its ends passes over into sections that are bent in the plane of the blank in opposite directions to form a blank having Z-shape. A coil spring made from the blank (in which the spring material as seen in cross section has radially flattened shape) at its ends has a lower pitch than the mid section or no pitch at all.

8 Claims, 1 Drawing Sheet

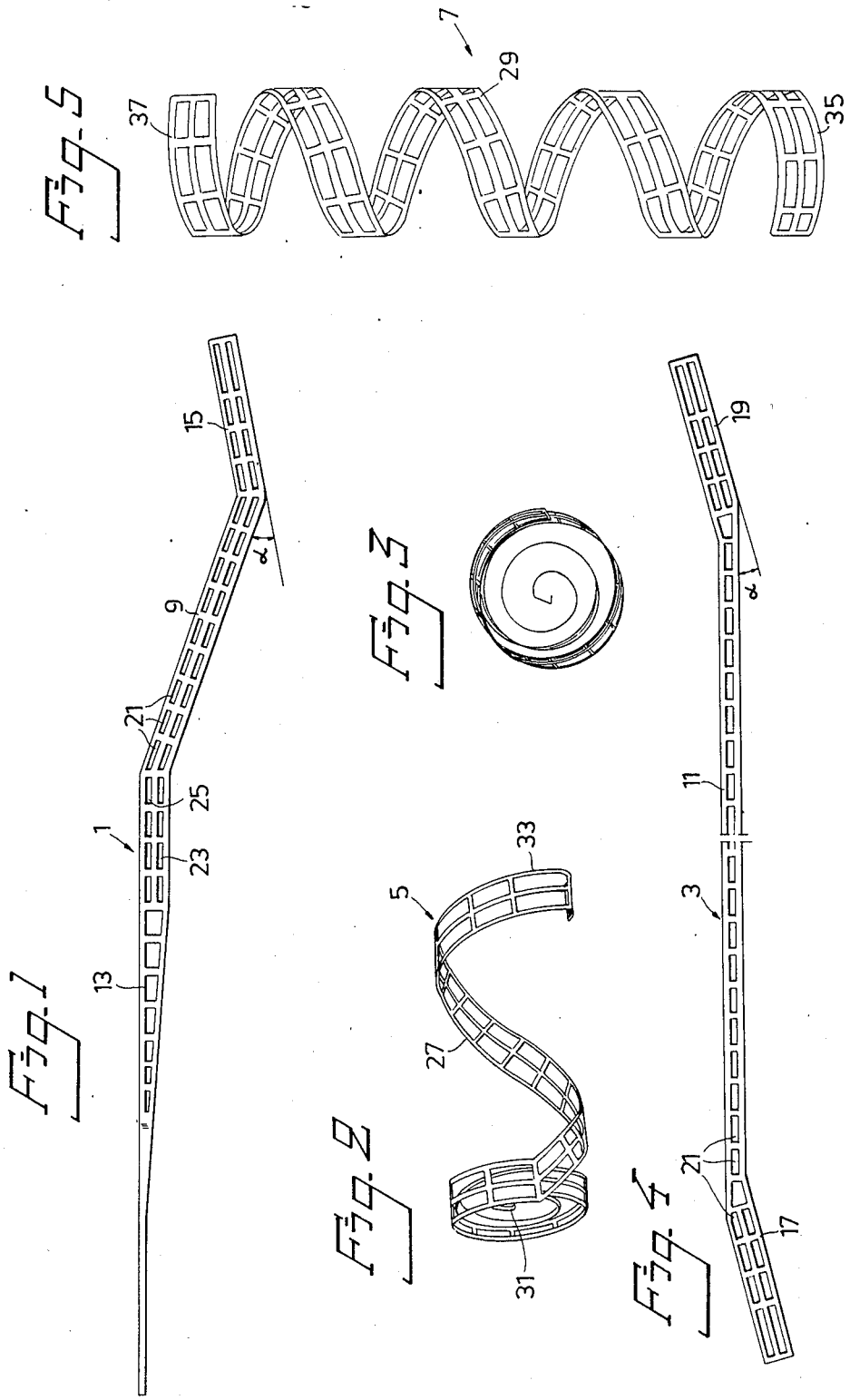

PLANAR BLANK AND A COIL SPRING MANUFACTURED THEREFROM

BACKGROUND AND SUMMARY OF THE INVENTION

The present invention relates to a planar blank intended for the manufacture of a coil spring. The coil spring being suitable for transluminal implantation. The invention also includes the coil spring being manufactured from the blank.

In surgical and other medicinal techniques there is often a need for being able to insert and expand devices in for example blood vessels, urinary tracts, respiratory tracts, intestinals or other difficultly accessible locations. The devices having for their function to widen the said vessel or duct and being capable of being left in position for providing permanent stability at the site of implantation.

In published British patent application No. 83 26791 there is disclosed a device which has for its purpose to provide the function indicated above. In this known device used for mechanical transluminal implantation, the prosthesis or spring means provides self-fixation by self-expansion at the site of implantation. There are, however, certain practical problems in connection with the transluminal displacement. When inserted into for example a blood vessel, the known coil spring is wound onto an elongated rod-shaped element and is there after released at the desired location in the body. In this operation it is essential that the coil spring surround the carrier body very closely so that the surrounding walls of the vessel will not be damaged during the transluminal movement of the device. It is also essential that the coil spring when released and expanded at the site of implantation will be anchored in a reliable manner so that it will not later move from its position at the site of implantation. The known device does not operate wholly satisfactorily in these two respects, and the present invention thus has for its purpose to provide an improved coil spring for transluminal implantation and a planar blank from which the coil spring is manufactured.

For this purpose the planar blank according to the present invention comprises an elongated, essentially straight midsection which, at opposite endsections is bent in a plane of the blank in opposite directions to form a blank having an approximate Z-shape. In this manner, a coil spring is made from the blank. At its end sections, the coil spring has a lower pitch than at the midsection of the coil spring and, in fact, the coil spring may have no pitch or substantially no pitch at all at its ends. By use of the planar bank, the material of the manufactured spring has a radially flattened shape, as seen in crossection.

For the purpose of enabling lower pitch and smaller distance between the turns in the midsection of the coil spring, the midsection of the blank can be made smaller than the endsections when viewed in the plane of the blank.

In order that the coil spring according to the invention, shall find use as a filter for thromboses, for example by application in *Vena Cava Inferior* to prevent formation of lungemboli, one endsection of the blank according to the invention can be extended as compared to the other endsection, so that when a coil spring is made from the blank several overlapping turns are formed. The turns, when viewed in a direction perpendicular to the centre line of the spring, lie essentially in the same plane. In this context it is preferred that one endsection be provided as an extended endsection and is made outwardly tapering for the purpose of reducing the flow resistance of the coil spring made from the blank.

In an alternative embodiment of the blank according to the invention, both endsections are substantially of equal length and have a length less than the length of a complete turn in the coil spring made from the blank when in an unloaded state. The endsection length is suitably less than about ¾ and preferably about ½ of said complete turn length.

The blank according to the invention is, preferably, over at least the major part of its length, provided with apertures extending in a direction perpendicular to the plane of the blank. The apertures are preferably arranged in at least one row extending in the longitudinal direction of the blank.

For providing a suitable shape of the coil spring made from the blank, the endsections of the blank are suitably bent over an angle ($\alpha$) lying within the range about 5°–40°, preferably about 10°–30° and particularly about 10°–25°.

The coil spring according to the present invention has an essentially helix shaped configuration, and its spring material as seen in an axial crossection is radially flattened. After being manufactured from the blank, the coil spring is characterized by a midsection having a circular cylindric shape and endsections having, in relation to the midsection, lower pitch or zero pitch. In a corresponding manner as the blank according to the invention said midsection of the coil spring may be made from material that is of an axially smaller dimension than the material of the endsections.

For use as a filter, the coil spring may have one endsection consisting of several turns which, in a direction perpendicular to the centre line of the coil spring lie in essentially the same plane, and which, in a direction towards the free end of the endsection have a progressively decreasing radius of curvature. In order to reduce the axial flow resistance of such coil spring the material of said one endsection is suitably made axially tapering in a direction extending towards the free end.

The coil spring according to the present invention may also be made substantially symmetrical, the material of the two endsections having essentially the same length which is less than a full turn of the spring and preferably less than ¾ turn of the spring.

For the purpose of facilitating the ingrowth of the coil spring in for example a blood vessel and thus to facilitate tissue growth the spring material over at least the major part of the spring is suitably provided with radially through-going apertures. It is particularly preferred that said openings have an area such that the main part of the remaining spring material has a tangential width of at most about 2.5 mm, preferably at most about 2 mm and particularly at most about 1.5 mm.

The material of the blank and the coil spring according to the present invention can be any medicinally acceptable material but is preferably constituted by a medicinally acceptable metal, for example of the type cobalt, chromium, nickel, molybdenum, iron alloy as defined in International Standard, ISO 5832/7-1984 (E). One example of such medicinally preferred metal alloy is Phynox ® which alloy contains nickel, chromium, molybdenum, cobalt, silicon and manganese in an amount of 18, 20, 7, 40, 0.3 and 1.5% by weight respectively.

The coil spring and the blank according to the present invention offer substantial advantages as compared to the prior art. Thus, the coil spring manufactured from the blank according to the invention may be easier manufactured by winding on to a mandrel of a suitable diameter as the bent endsections enable flat and even winding on to the mandrel. Moreover, the coil spring in transluminal implantation offers the major advantage that it can be wound on to a tubular or rod-shaped body to tight engagement thereon so that the transluminar displacement can be carried out without damages to surrounding tissue.

With regard to the thickness of the planar blank according to the invention it is, of course, dependent on the size of the coil spring to be manufactured and may therefor vary within broad limits. However, the preferred thickness range is about 0.05 to 0.7 mm, preferably up to 0.5 mm. A particularly useful thickness range is about 0.1 to about 0.3 mm.

BRIEF DESCRIPTION OF THE DRAWINGS

The invention will now be further described with reference to non-limiting examples and to the appended drawing, wherein:

FIG. 1 shows an embodiment of the blank according to the invention;

FIG. 2 shows in a sideview a coil spring made from the blank of FIG. 1, whereas

FIG. 3 shows the same spring in an endview;

FIG. 4 shows another embodiment of the blank according to the invention; and

FIG. 5 shows in a sideview a coilspring manufactured from the blank of FIG. 4.

DETAILED DESCRIPTION OF THE INVENTION

The blank shown in FIG. 1 and generally indicated at 1 has a straight midsection 9 and an elongated endsection 13 bent in relation to the midsection 9, and another endsection 15 bent in relation to the midsection 9 in the opposite direction. The blank thereby forms somewhat a straightened Z-shape. Over the major part of its length blank 1 is provided with through-going apertures 21, which in the embodiment shown form two longitudinally extending rows 23,25 in the midsection, one endsection 15 and along a part of the other endsection 13. The elongated endsection 13 is made outwardly tapering for a purpose to be further explained below.

In FIGS. 2 and 3 there is shown a coil spring made from the blank of FIG. 1 and generally designated 5. This coil spring has, in a manner corresponding to that of the blank from which it was manufactured a midsection 27 and endsections 31,33, of which the endsection 31 corresponding to the elongated endsection 13 of the blank of FIG. 1 and forms a spiral lying in one plane having a progressively decreasing radius of curvature towards the centre (see FIG. 3). The other endsection is constituted by about half a springturn with a pitch which is substantially zero.

The coil spring shown in FIG. 2 may thus be used as a filter for thromboses in bloodvessels, for example by application in *Vena Cava Inferior* so that one may thereby prevent formation of lungemboli. By the elongated endsection 13 being provided with a tapering shape there is obtained the advantage that the axial resistance to flow of the coil spring will be reduced in a direction extending towards the centreline of the coil spring. In this manner unacceptable deviation of the filterpart 31 of coil spring 5 when blood flows through the coil spring will be prevented. By designing the coil spring with endsections 31,33 having a pitch of zero, the spring obtains in connection with its implantation, a more stable anchorage in the surrounding walls of the vessel and collapse of the spring will thus effectively be prevented. By designing the spring with the throughgoing apertures 21 the tissue growth in the surrounding walls of the vessel will be substantially facilitated.

The blank of the invention shown in FIG. 4 and generally designated 3 consists in a similar manner of a midsection 11 and endsections 17,19. The blank is, moreover, provided with through-going apertures 21 as in FIG. 1. In the embodiment shown a midsection 11 is provided with lower or less width than the endsections 17, 19 in order to enable winding with closer turns and thus lower pitch in the coil spring made from the blank.

In FIG. 5 there is shown a coil spring manufactured from the blank of FIG. 4 consisting of a midsection 29 and endsections 35,37, the later sections having a pitch of about zero. The length of each of these endsections 35,37 is about one half-turn of the spring.

The embodiment of the invention shown in FIGS. 4 and 5 offers the same advantages as the filtervariant described in FIGS. 1-3 and may advantageously be used in transluminar implantation for example to support deficit bloodvessels or to stabilize respiratory tract and bronci.

It should be observed that the invention is not limited to the embodiments described above which are solely intended to illustrate the invention, the invention being limited only by the scope of the appended patent claims.

I claim:

1. A coil spring for intraluminal implantation and having an essentially helix-shaped configuration, the spring material being radially flattened as seen in an axial cross section and comprising a mid section of circular cylindric shape and two integral end sections having, relative to the mid section, lower pitch, one end section consists of several turns which, in a direction perpendicular to the centre line of the coil spring, lie in essentially a common plane and which in a direction towards a free end of said one end section have a progressively decreasing radius of curvature.

2. A coil spring according to claim 1, wherein the material of said one end section is axially tapering towards the free end so as to reduce axial flow resistance of the coil spring.

3. A coil spring according to claim 1, wherein the spring material over at least a major part of the spring is provided with radially through-going apertures.

4. A coil spring according to claim 3, wherein said apertures cover an area so that remaining spring material has a tangential width of at most 2.5 mm.

5. A coil spring for intraluminal implantation and having an essentially helix-shaped configuration, the spring material being radially flattened as seen in an axial cross section and comprising a midsection of circular cylindric shape and two integral end sections having relative to the midsection, lower pitch;
   wherein the material of the two end sections has essentially the same length, said length corresponding to less than a full turn of the spring.

6. A coil spring according to claim 5, wherein said mid section is made from an axially smaller material than material of the end sections.

7. A coil spring according to claim 4, wherein the end sections each extend over less than about ¾ turn.

8. A coil spring according to claim 5, wherein the end sections each extend over less than about ¾ turn.

* * * * *